United States Patent [19]

Shibanai

[11] Patent Number: 4,769,242

[45] Date of Patent: * Sep. 6, 1988

[54] PROCESS FOR PREPARING INSECT-REPELLANT AND INSECTICIDAL ARTICLE FOR BREEDING PLANTS

[75] Inventor: Ichiro Shibanai, Tokyo, Japan

[73] Assignee: Japan Liquid Crystal Co., Ltd., Tokyo, Japan

[*] Notice: The portion of the term of this patent subsequent to Jan. 13, 2004 has been disclaimed.

[21] Appl. No.: 803,267

[22] Filed: Nov. 29, 1985

[30] Foreign Application Priority Data

Dec. 11, 1984 [JP] Japan ................... 59-260005

[51] Int. Cl.⁴ .................. A61K 1/02; C08K 5/13
[52] U.S. Cl. .................. 424/411; 424/409; 424/83; 514/58; 264/117; 264/122; 264/125
[58] Field of Search ............ 264/117, 122–125; 424/83, 411, 409; 514/58

[56] References Cited

U.S. PATENT DOCUMENTS

| | | | |
|---|---|---|---|
| 3,005,720 | 10/1961 | Teller | 424/83 |
| 3,318,769 | 5/1967 | Folckemer et al. | 424/83 |
| 3,661,838 | 5/1972 | Enomoto | 424/83 |
| 3,987,007 | 10/1976 | Kalogris | 523/122 |
| 4,356,115 | 10/1982 | Shibanai et al. | 252/522 A |

FOREIGN PATENT DOCUMENTS 0150577 9/1983 Japan.

OTHER PUBLICATIONS

Kariya, A., CA. 88, #46331d (1978).
Yamamoto et al., CA. 87, #113013w (1977).
Mifune et al., CA. 82, #39586p (1975).
Takeda, CA. 96, #16093a (1982).
Miyamoto et al., CA. 82, #107568m (1975).
Yamamoto et al., CA. 86, #127142 (1977).

*Primary Examiner*—Morton Foelak
*Assistant Examiner*—S. A. Acquah
*Attorney, Agent, or Firm*—Jordan and Hamburg

[57] ABSTRACT

A process for preparing an insect-repellent and insecticidal article for breeding plants including forming a clathrate compound consisting of an organophosphorus or a pyrethroid insecticide included in cyclodextrin; mixing the clathrate compound with a synthetic resin compound and molding the mixture into an article for breeding plants.

10 Claims, No Drawings

PROCESS FOR PREPARING INSECT-REPELLANT AND INSECTICIDAL ARTICLE FOR BREEDING PLANTS

BACKGROUND OF THE INVENTION

This invention relates to a process for preparing an insect-repellent and insecticidal synthetic resin article for breeding plants wherein an organophosphorus or a pyrethroid insecticide is used as an insect-repellent and insecticidal agent.

Insecticides have been used in breeding plants to prevent insect damage. They are previously applied on soil or applied or sprayed onto plants during cultivation. These insecticides have been directly applied or sprayed by men.

It is not preferable for the health of a worker to apply or spray insecticides. Further, such operations are highly affected by the weather. That is, it is difficult to get a prolonged insecticidal effect because of rain and wind. Thus it is necessary to repeat application of insecticides during cultivation of plants.

SUMMARY OF THE INVENTION

Under these circumstances, the process for preparing an insect-repellent and insecticidal article for breeding plants according to the present invention comprises forming a clathrate compound consisting of an organophosphorus or a pyrethroid insecticide includes in cyclodextrin or a starch hydrolyzate containing cyclodextrin; drying and powdering the obtained clathrate compound; melting 0.1 to 50% by weight of the powder together with a synthetic resin compound; pelletizing the obtained mixture and molding the pellets optionally with an appropriate amount of the synthetic resin into the desired shape. In this process, the organophosphorus or pyrethroid insecticide, i.e., an insect-repellent and insecticidal agent is used in the form of a clathrate compound included in cyclodextrin to uniformly mix the insecticide with the synthetic resin and to give an appropriate bleeding of the pyrethroid insecticide on the surface of the film. Detailed Description of the Preferred Embodiments:

An example of the organophosphorus insecticide used in the present invention is fenitrothion [O,O-dimethyl O-(3-methyl-4-nitrophenyl) thiophosphate]:

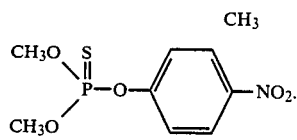

The pyrethroid insecticide used in the present invention includes the following:

allethrin [dl-3-allyl-2-methyl-4-oxo-2-cyclopentenyl dl-cis/trans-chrysanthemate]:

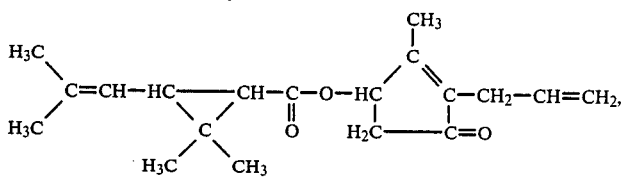

phethlthrin [(1,3,4,5,6,7-hexahydro-1,3-dioxo-2-isoindolyl)methyl dl-cis/trans-chrysanthemate]:

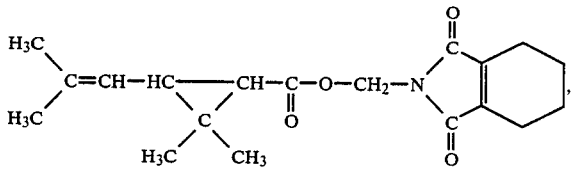

resmethrin [(5-benzyl-3-furyl)methyl dl-cis/trans-chrysanthemate]:

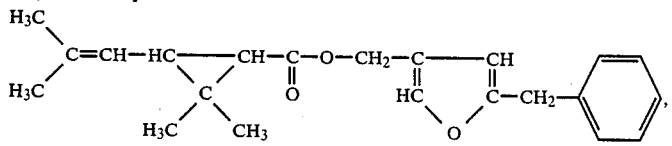

furamethrin [(5-(2-propinyl)-2-furyl)methyl dl-cis/trans-chrysanthemate]:

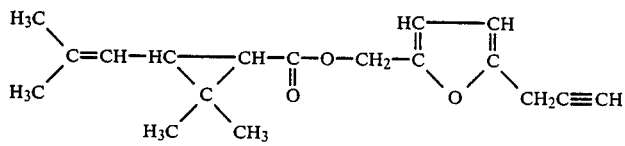

phenothrin [(3-phenoxybenzyl d-cis/trans-chrysanthemate]:

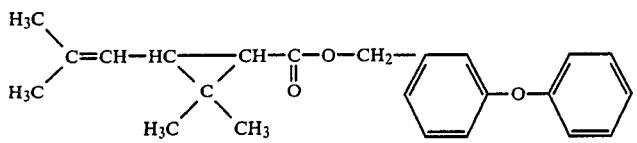

permethrin [3-phenoxybenzyl dl-cis/trans-3-(2,2-dichlorovinyl(2,2-dimethyl-1-cyclopropanecarboxylate]:

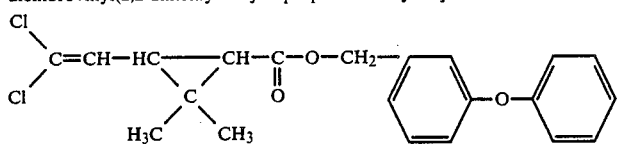

In the process of the present invention, an organophosphorus or a pyrethroid insecticide is used as an insect-repellent and insecticidal agent since it exhibits an excellent effect as well as a low toxicity and is available over a wide range. Further, it can be readily included in cyclodextrin to thereby form a clathrate compound. Furthermore, it is relatively stable at high temperatures so that it can be mixed with a synthetic resin compound for molding.

The cyclodextrin used in the present invention is a particular dextrin wherein D-glucose molecules form a ring by binding to each other through an $\alpha$-1,4 linkage and characterized by having a doughnut-like molecular structure with an inner cavity of 6 to 10 Å in diameter. Cyclodextrin can be classified into three types (i.e. $\alpha$-, $\beta$- and $\gamma$-cyclodextrins) depending on the number of constituting D-glucose units. Any of these types can be used in the present invention. For example, $\beta$-cyclodextrin is in the form of a white crystalline powder and represented by the molecular formula $(C_6H_{10}O_5)$, has a molecular weight of 1135 and melts at 300° to 305° C. (dec.)

In the process of the present invention, the cyclodextrin may be substituted by a starch hydrolyzate containing cyclodextrin obtained by various methods. For example, a starch hydrolyzate of the above type can be obtained as an intermediate in the preparation of cyclodextrin by hydrolyzing starch with cyclodextrin synthetase produced by a microorganism belonging to tne genus Bacillus. The process for the preparation of the starch hydrolyzate will be further described in detail.

A starch solution is adjusted to a pH value of 10, homogeneously gelatinized and allowed to cool. Then cyclodextrin glycosyltransferase, which is a fermentation product of a microorganism selected from Bacillus No. 13, No. 17-1, No. 38-2, No. 135 and No. 169 strains, has an optimum pH value in a basic region and exhibits a high thermal stability, is added thereto to effect a reaction. The reaction mixture is heated to inactivate the enzyme and allowed to cool. Then it is adjusted to a pH value of 5.0. Commercially available glucoamylase is added thereto to thereby decompose unreacted matters.

Subsequently the mixture is filtered in a conventional manner and concentrated to give a cyclodextrin concentration of approximately 40 % or above. A small amount of seed cyclodextrin is added to the concentrate and allowed to stand. The cyclodextrin thus precipitated is filtered and dried to give $\beta$-cyclodextrin. The filtrate obtained at this stage is the desired starch hydrolyzate (cf. Japanese Patent Publication No. 43897/1977).

The bacillus No. 13, No. 17-1, No. 38-2, No. 135 and No. 169 strains as described above have been deposited with the Fermentation Research Institute of the Agency of Industrial Science and Technology and referred to as FERM No. 611, No. 612, No. 614, No. 617 and No. 618, respectively.

A commercially available starch syrup containing cyclodextrin prepared by repurifying the abovementioned filtrate with an ion exchange resin followed by concentration may be used in the process of the present invention.

The starch hydrolyzate containing cyclodextrin used in the present invention is not restricted to those obtained by the above processes but a starch hydrolyzate containing $\alpha$-, $\beta$- or $\gamma$-cyclodextrin or a mixture thereof obtained by any process may be employed.

The synthetic resin compound used in the present invention should have a low melting point. This is because the organophosphorus or pyrethroid insecticide would decompose above 180° C. although it is heat resistant. Some synthetic resins are molded at a temperature higher than 180° C. so that it is necessary to select a synthetic resin compound which can be molded at a temperature lower than the decomposing point of the organophosphorus or pyrethroid insecticide. Thus synthetic resin compounds such as an olefinic plastic, a flexible vinyl chloride plastic or a vinyl acetate plastic may be employed.

Now examples of the process for the preparation of the insect-repellent and insecticidal apparatus for breeding plants according to the present invention will be given.

EXAMPLE 1

85 parts by weight of $\alpha$-cyclodextrin was added to 15 parts by weight of fenitrothion and the mixture was stirred at 50° C. for one hour. The clathrate compound consisting of fenitrothion included in cyclodextrin thus obtained was ground with a vacuum drier at 60° C. to give a powder of 150 mesh or below. 50 parts by weight of this powder was formed into a molten mixture together with 50 parts by weight of a flexible vinyl chloride compound. The molten mixture was pelletized by cold-cutting. Then 10 parts by weight of the pellets were mixed with 90 parts by weight of the flexible vinyl chloride compound and the mixture was molded into a pipe by extruding. Thus a bar for breeding plants was prepared.

EXAMPLE 2

90 parts by weight of β-cyclodextrin was added to 10 parts by weight of phthalthrin and the mixture was stirred at 50° C. for one hour. The clathrate compound consisting of phthalthrin included in cyclodextrin thus obtained was ground with a spray drier at 60° C. to give a powder of 150 mesh or below. 30 parts by weight of this powder was formed into a molten mixture together with 70 parts by weight of a flexible vinyl chloride compound. The molten mixture was pelletized by hot-cutting. Then 20 parts by weight of the pellets were mixed with 80 parts by weight of the flexible vinyl chloride compound and the mixture was molded into a hose by extruding.

EXAMPLE 3

85 parts by weight of a starch hydrolyzate containing 50 % of α-, β- and γ-cyclodextrins was added to 15 parts by weight of resmethrin and the mixture was stirred at 50° C. for one hour. The clathrate compound consisting of resmethrin included in cyclodextrin thus obtained was ground with a vacuum drier at 60° C. to give a powder of 150 mesh or below. 20 parts by weight of this powder was formed into a molten mixture together with 80 parts by weight of polyethylene pellets. The molten mixture was molded into pellets by cold-cutting and subsequently into a pot by extruding.

EXAMPLE 4

85 parts by weight of a starch hydrolyzate containing 15% of α-, β- and γ-cyclodextrins was added to 15 parts by weight of furamethrin and the mixture was stirred at 50° C. for one hour. The clathrate compound consisting of furamethrin included in cyclodextrin thus obtained was ground with a spray drier at 60° C. to give a powder of 150 mesh or below. 10 parts by weight of this powder was formed into a molten mixture together with 90 parts by weight of a vinyl acetate compound. The molten mixture was pelletized by underwater-cutting. 40 parts of the pellets were mixed with 60 parts by weight of the vinyl acetate compound and the mixture was molded into a bag by inflating. Thus a protective bag for fruits was prepared.

EXAMPLE 5

80 parts by weight of α-cyclodextrin was added to 20 parts by weight of phenothrin and the mixture was stirred at 50° C. for one hour. The clathrate compound consisting of phenothrin included in cyclodextrin thus obtained was ground with a drum drier to give a powder of 150 mesh or below. 10 parts by weight of this powder was formed into a molten mixture together with 90 parts by weight of an ethylene-vinyl acetate compound. The molten mixture was molded into pellets by sheet-cutting and subsequently into a film by extruding.

EXAMPLE 6

85 parts by weight of a starch hydrolyzate containing 50 % of α-, β- and γ-cyclodextrins was added to 15 parts by weight of permethrin and the mixture was stirred at 50° C. for one hour. The clathrate compound consisting of permethrin included in cyclodextrin thus obtained was ground with a vacuum drier at 60° C. to give a powder of 150 mesh or below. 20 parts of this powder was formed into a molten mixture together with 80 parts by weight of polyethylene pellets. The molten mixture was pelletized by cold-cutting. Then the pellets were molded into a planter by extrusion.

EXAMPLE 7

90 parts by weight of β-cyclodextrin was added to 10 parts by weight of allethrin and the mixture was stirred at 50° C. for one hour. The clathrate compound consisting of allethrin included in cyclodextrin thus obtained was ground with a spray drier at 60° C to give a powder of 150 mesh or below. 30 parts by weight of this powder was formed into a molten mixture together with 70 parts by weight of a flexible vinyl chloride compound. The molten mixture was pelletized by hot-cutting. Then 20 parts by weight of the pellets were mixed with 80 parts by weight of the flexible vinyl chloride compound and molded into a watering pot by blowing.

Each insect-repellent and insecticidal article for breeding plants thus prepared exhibited a uniform insect repellent and insecticidal effect. In addition, the appropriate bleeding of the insecticide on the surface of the molded article allowed this effect to persist for a prolonged period. These insect-repellent and insecticidal article for breeding plants thus obtained may be used in the following manner.

APPLICATION EXAMPLE 1

Insect-repellent and insecticidal pots and planters exhibit an insecticidal effect on soil so that no insecticidal treatment of the soil is required.

APPLICATION EXAMPLE 2

Insect-repellent and insecticidal bars used as props for plants exhibit a similar effect as those obtained by directly applying insecticides on the plants so that no insecticidal operation during the cultivation is required.

APPLICATION EXAMPLE 3

When water is sprinkled through an insect-repellant and insecticidal hose or watering pot, the insecticide contained therein gradually bleeds into the water so that it is unnecessary to add an insecticide thereto.

As described above, the process for preparing an insect-repellent and insecticidal article for breeding plants according to the present invention, which comprises forming a clathrate compound consisting of an organophosphorus or a pyrethroid insecticide included in cyclodextrin, mixing the clathrate compound with a synthetic resin compound and molding the mixture into the desired shape, can give an article exhibiting a uniform insect-repellent and insecticidal effect because of the uniform dispersion of the insecticide therethrough. Further, the insect-repellent and insecticidal effect of this apparatus can persist for a prolonged period because of the appropriate bleeding of the insecticide on its surface. The desired intensity of the insect-repellent and insecticidal effect can be obtained by selecting an appropriate pyrethroid insecticide and/or varying the amount of the insecticide or pellets depending on the insects to be exterminated.

What is claimed is:

1. A process for preparing an insect-repellent and insecticidal article for breeding plants which comprises forming a clathrate compound consisting of fenitrothion (O,O-dimethyl O-(3-methyl-4-nitrophenyl) thiophosphate) or a pyrethroid insecticide included in cyclodextrin or a starch hydrolyzate containing cyclodextrin; drying and powdering the obtained clathrate compound; melting 0.1 to 50% by weight of the obtained powder together with a synthetic resin compound which can be molded at a temperature lower than the decomposition temperature of the fenitrothion or pyrethroid insecticide; pelletizing the mixture and molding the pellets into the shape of a desired article at a temperature lower thant the decomposition temperature of the fenitrothion or pyrethroid insecticide.

2. A process for preparing an insect-repellent and insecticidal article for breeding plants as set forth in claim 1 wherein said insecticide is permethrin (3-phenoxybenzyl dl-cis/trans-3-(2,2-dichlorovinyl(2,-dimethyl-1-cyclopropanecarboxylate.

3. A process for preparing an insect-repellent and insecticidal article for breeding plants as set forth in claim 1 wherein said synthetic resin compound is polyethylene.

4. A process for preparing an insect-repellent and insecticidal article for breeding plants as set forth in claim 1 wherein said article comprises a bar for breeding plants.

5. A process for preparing an insect-repellent and insecticidal article for breeding plants as set forth in claim 1 wherein said article comprises a hose.

6. A process for preparing an insect-repellent and insecticidal article for breeding plants as set forth in claim 1 wherein said article comprises a pot.

7. A process for preparing an insect-repellent and insecticidal article for breeding plants as set forth in claim 1 wherein said article comprises a protective bag for fruit.

8. A process for preparing an insect-repellent and insecticidal article for breeding plants as set forth in claim 1 wherein said article comprises a planter.

9. A process for preparing an insect-repellent and insecticidal article for breeding plants as set forth in claim 1 wherein said article comprises a watering pot.

10. A process for preparing an insect-repellent and insecticidal article for breeding plants as set forth in claim 1 wherein said pellets are molded with an additional amount of synthetic resin compound to form said desired article.

* * * * *